United States Patent [19]

Lauk

[11] Patent Number: 4,695,277
[45] Date of Patent: Sep. 22, 1987

[54] PHARMACEUTICAL ADHESIVE PLASTER AND METHOD FOR MANUFACTURING IT

[75] Inventor: Willi Lauk, Schorndorf-Haubersbronn, Fed. Rep. of Germany

[73] Assignee: Allpack Industrielle Lohnverpackung GmbH & Co. KG, Fed. Rep. of Germany

[21] Appl. No.: 766,420

[22] Filed: Aug. 16, 1985

[30] Foreign Application Priority Data

Aug. 17, 1984 [DE] Fed. Rep. of Germany ....... 3430250
Apr. 2, 1985 [DE] Fed. Rep. of Germany ....... 3511963

[51] Int. Cl.$^4$ .............................................. A61F 13/00
[52] U.S. Cl. .................................... 604/304; 604/897; 128/156
[58] Field of Search ................................ 604/304–308; 206/484.1, 484.2, 531, 532, 534.2; 607/890, 897; 424/28

[56] References Cited

U.S. PATENT DOCUMENTS

| 4,379,454 | 4/1984 | Campbell et al. | 604/897 |
| 4,486,193 | 12/1984 | Shaw et al. | 604/890 |
| 4,573,996 | 3/1986 | Kwiatek et al. | 604/897 |

FOREIGN PATENT DOCUMENTS

| 0008545 | 3/1980 | European Pat. Off. | 206/534.2 |
| 0013606 | 7/1980 | European Pat. Off. | |
| 0126059 | 9/1980 | Japan | 206/484 |

Primary Examiner—C. Fred Rosenbaum
Assistant Examiner—Jerome R. Smith, Jr.
Attorney, Agent, or Firm—Wigman & Cohen

[57] ABSTRACT

In order that, in a plaster comprising a composite film having a recess for holding the medicament and having a layer of adhesive surrounding the recess and a composite covering film glued to the recess and covering it, the galenical may be optimized regardless of the properties of a matrix containing the medicament in the recess, it is proposed to close the recess by means of a membrane which is firmly connected to the composite film and is permeable to the active ingredient of the medicament, and to join the composite covering film hermetically to the composite film along a ring extending between the central membrane and the surrounding layer of adhesive.

To provide a process for the production of such a plaster in which two separately produced, outer parts of the plaster are joined together in a separable manner by means of an inner layer of adhesive, which process should be capable of rational mass production of the plaster, it is proposed to produce the layer of adhesive as a component of an inner, third part of the plaster, which is produced separately from the two outer parts of the plaster and is subsequently firmly connected to these outer parts.

1 Claim, 4 Drawing Figures

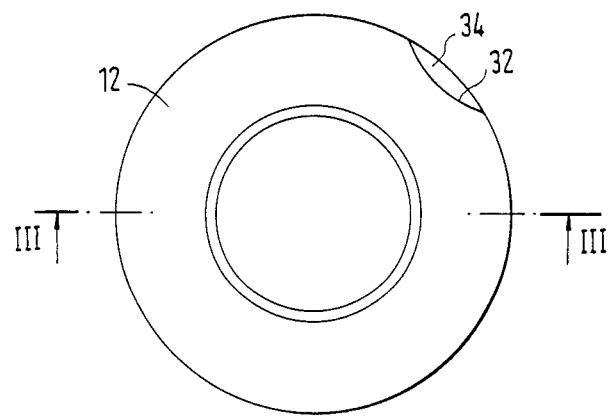
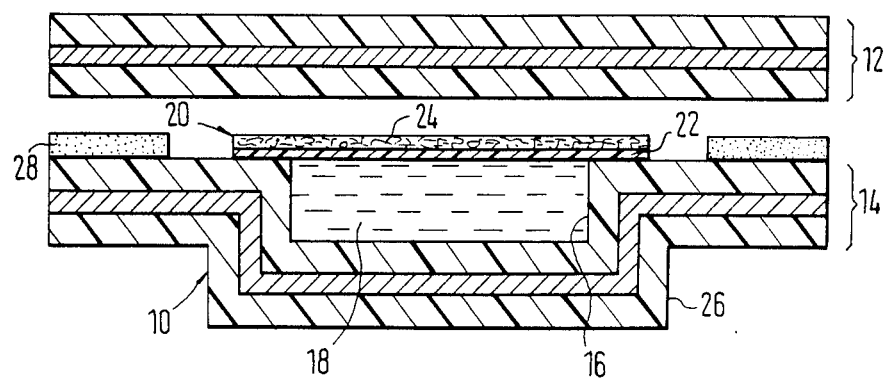
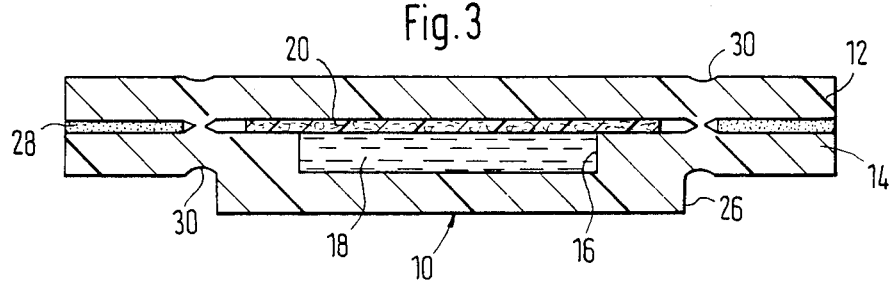

PHARMACEUTICAL ADHESIVE PLASTER AND METHOD FOR MANUFACTURING IT

BACKGROUND OF THE INVENTION

This invention relates to a pharmaceutical adhesive plaster composed of at least two parts joined together, of one part which contains the active ingredient and consists of a composite film with a shallow recess for containing the medicament. Optionally, it can have an innermost layer of a thermoplastic synthetic resin, in particular in the form of a film, and an outer layer of adhesive which is pressure-sensitive and/or sensitive to the heat of the skin (skin compatible) surrounding the recess in the form of a ring on the opening side of the recess. The other part consists of a composite film serving as a covering, optionally with an innermost layer of a thermosplastic synthetic resin, in particular in the form of a film, which covering is joined to the adhesive layer and covers the recess of the part containing the active ingredient; in other words, a so-called transdermal therapeutic system.

In a medicinal plaster of this kind disclosed in European publication No. 0 013 606 A 2, the medicament which contains or constitutes the active ingredient and diffuses into the skin is distributed in a so-called diffusion matrix embedded in the recess of the part for containing the active ingredient. The composite covering film of the known plaster is provided on its internal surface with a so-called separating layer which corresponds to the layer of adhesive and from which the layer of adhesive can easily be detached when the covering film is separated from the active ingredient container. The diffusion matrix is either inserted in the recess of the composite film containing the active ingredient or is poured into this recess and solidified therein.

One of the main disadvantages of this arrangement is that the so-called galenical, that is to say the preparation of active ingredient in the medicament, depends on the properties of the chosen matrix so that these properties must be taken into account, with the result that it is difficult to optimize the galenical.

It is therefore an object of the present invention to provide a pharmaceutical adhesive plaster in which this first disadvantage is overcome and which enables the galenical to be optimized independently of the properties of the matrix.

In a plaster of the type defined above, this problem is solved according to the invention by means of the fact that the recess of the active ingredient container is closed by a membrane which is permeable to the active ingredient and firmly connected to the composite film of the active ingredient container and that the composite film constituting the covering is hermetically connected to the composite film of the active ingredient container along a ring extending between the membrane and the layer of adhesive.

This has the advantageous result of providing a completely free choice of galenical for which a suitable membrane can be selected, this membrane serving to retain the medicament in the recess of the active ingredient container while enabling it to be gradually transmitted to the skin.

The known plaster, which is hermetically sealed in a flat bag until required for use, has the further disadvantage that the diffusion matrix is not capable of completely delivering to the skin all the medicament or active ingredient contained in it, especially that contained at the bottom of the recess because this portion must first itself diffuse through the matrix before it can diffuse into the skin in contact with the matrix. The dose provided by the container is therefore insufficient unless an appropriate excess of medicament has from the start been introduced into the matrix, but this procedure in some cases considerably increases the cost of production. The use of the known plaster may thus result in incorrect dosage of the medicament applied.

It is therefore a further object of the present invention to provide a pharmaceutical adhesive plaster which overcomes this disadvantage and results in virtually correct dosage due to almost complete exhaustion of the medicament. In a plaster of the type defined above, this problem is solved according to the invention by means of the fact that the recess of the active ingredient container only contains the medicament which constitutes or contains the active ingredient and which diffuses into the skin, this recess being most preferably closed by the membrane which is permeable to the active ingredient and firmly attached to the composite film of the active ingredient container. In this arrangement, the composite film forming the covering is hermetically attached to the composite film of the active ingredient container along the ring between the membrane and the layer of adhesive. The term "hermetic" is used to denote that no air can enter the interior of the plaster and no active ingredient can leave the interior.

The advantageous result is thereby achieved that the medicament, which can be constantly given off to the skin in small quantities while the mass of medicament is held back by the membrane, which is semi-permeable or may have been rendered diffusible, for example, by perforation, can be used up almost completely, no significant residues being left in the active ingredient container. This not only greatly facilitates accurate dosing of the medicament but also enables it to be carried out more economically since it is. now not necessary to provide for an excess when a minimum dosage is required. Furthermore, it is now unnecessary to provide a separate envelope for the plaster since the parts of the plaster are not only glued together but also welded.

In DE-U- No. 84 24 387 (ALLPACK) it has already been proposed to solve the last mentioned problem in a pharmaceutical adhesive plaster of the type defined above by filling the recess of the active ingredient container only with the medicament containing or constituting the active ingredient which diffuses into the skin and covering the recess with a membrane which is permeable to the active ingredient and is firmly attached to the composite film of the active ingredient container, and by hermetically connecting the composite film of the covering to the composite film of the active ingredient container along a ring between the membrane and the layer of adhesive, the said covering film optionally lying with its flat surface in direct contact with the layer of adhesive. In that case, a preferred embodiment of the plaster according to the invention differs from the plaster previously proposed in that composite film forming the covering is indirectly in contact by its flat internal surface with the layer of adhesive which forms part of a third part of the plaster forming a ring round the recess containing active ingredient. This third component of the plaster is firmly connected both to the composite film of the active ingredient container and to the composite film of the covering and can be separated into two parts along the sticky side of the layer of adhesive facing the covering, this separation into two parts exposing the said adhesive surface.

By providing this third part of the plaster next to the membrane and in addition to the active ingredient container and the covering film, it is most easily possible to provide the most suitable material conditions for separating the covering from the ingredient container to expose the layer of adhesive and the membrane because the two components of the third part of the plaster, one of which carries the layer of adhesive and the other a counter-layer, may themselves be composed of a plurality of layers so that it is possible to choose the most suitable combination of materials for the pairs of layers to be joined together, including also at the boundaries between the third plaster part and the composite film of the active ingredient container and between the third plaster part and the covering film.

SUMMARY AND OBJECT OF THE INVENTION

In the preferred embodiment of the plaster according to the invention, the membrane consists, as does also the third part of the plaster, of at least three layers, one of which is arranged as an adhesive layer between the two other layers. This ensures that the adhesive surface of the layer of adhesive which is to be brought into contact with the skin is always protected from unwanted contact before separation of the lower part of the third plaster part adhering thereto.

The preferred embodiment is distinguished by the fact that the membrane and the third plaster part are each composed of a thermoplastic layer of synthetic resin which is welded to a thermoplastic layer of synthetic resin of the composite film of the active ingredient container, a layer of adhesive applied to the first mentioned layer, a thermoplastic layer of synthetic resin welded to the layer of thermoplastic resin of the covering film and, applied to the aforesaid layer of synthetic resin, another layer, preferably of silicone, which lies in contact with the layer of adhesive. Both this layer and the synthetic resin layer of the membrane which is connected to the composite film of the active ingredient container are permeable to the active ingredient, and the silicone layer and/or the plastics layer of the membrane connected to the covering film is optionally impermeable to the active ingredient. One of these alternative conditions would have to prevail if the composite covering film were itself permeable to the active ingredient, which would appear to be unsuitable. The fact that both the membrane and the third part of the plaster have the same sequence of layers is an advantage in the manufacture and use of the plaster. A four-layered structure of membrane and third plaster part would appear to be sufficient.

In the preferred embodiment, the composite film containing active ingredient has an elevation surrounding its recess and situated outside the membrane and within the third plaster part and/or the composite covering film has a corresponding elevation, the height of which, alone or together with the other elevation, corresponds to the thickness of the third plaster part and of the membrane. As a result, the composite covering film does not undergo any significant deformation when it is welded to the composite film of the active ingredient container for the purpose of hermetically joining the two together along the ring between the membrane and the concentric, third plaster part, with the result that lettering applied to the outside, such as instructions for use, remains clearly legible even in the region of the aforementioned ring.

In another embodiment of the pharmaceutical adhesive plaster according to the invention which is advantageous in another respect, the membrane and the third part of the plaster are made in one piece so that it is not necessary to provide an elevation on the film of active ingredient container or on the covering film to provide contact between the film of active ingredient container and the composite covering film, which may initially be flat. This formation of the membrane and third part of the plaster in a single piece not only provides for a more rational manufacture of the plaster but also ensures that the composite covering film can easily be separated from the active ingredient container because it is now not necessary to tear open a weld between the active ingredient container film and covering film at the elevation or elevations, no matter how narrow the ring of hermetic seal.

In the preferred embodiment, a portion of plaster composed of the composite covering film and the lower component of the third plaster part rigidly attached to this covering film is separated off at the edge by means of a separating furrow, this separate portion of plaster lying on the layer of adhesive of the other lower component of the third plaster part and adhering thereto. By gripping the plaster with both hands on either side of the separating furrow, and bending the plaster round the furrow, the layer of adhesive can easily be exposed in the region of the furrow. Once a start has been made, the covering film with the lower component of the third plaster part adhering thereto can be completely separated from the remaining lower part to expose the adhesive surface of the layer of adhesive.

In another embodiment of the pharmaceutical adhesive plaster according to the invention, in which the film containing the active ingredient definitely has a layer of thermoplastic synthetic resin facing the composite covering film as in the case of the known plaster, the semipermeable membrane is a composite material composed of a porous, thermoplastic layer of synthetic resin welded to the synthetic resin layer of the composite film of the active ingredient container and a layer of fibrous web which is impregnated with glycerol and forms a surface for contact with skin. Membranes of this kind are available commercially for ultrafiltration and it is only necessary to select one which is most suitable for effective diffusion of the active ingredient. The impregnation with glycerol is not absolutely necessary.

In the other embodiment, in which the composite films are both covered with a film of thermoplastic synthetic resin on the sides facing each other, as in the known plaster, these two films are welded together to provide a hermetic connection between the composite covering film and the active ingredient container. The technique of heat sealing is well known and can be carried out without difficulty. One of the films of synthetic resin may be replaced by a layer of sealing wax which could possibly bond more readily to the other film.

In other embodiment, a separating furrow is provided on the covering film to divide off a piece at the edge, this piece extending down into the layer of adhesive and adhering completely to this layer so that the plaster can be gripped by thumb and forefinger of one hand in the region of this separate piece and a fingernail of the other hand can be placed under the edge of the covering film at the separating furrow, whereupon the greater part of the covering film can be stripped from the active ingredient container with this other hand, only the piece at the edge being left in place, but this piece need not necessarily be removed from the active ingredient container since part of the layer of adhesive is also active between the piece at the edge and the recess in the active ingredient container.

To prevent the layer of adhesive drying out due to evaporation of solvent, the composite covering film may be hermetically sealed to the film of the active ingredient container along a ring at the edge of the plaster, outside the layer of adhesive. Instead of providing the arrangement described above for opening the plaster, the composite covering film and the film containing the active ingredient may by designed to form projecting opening flaps outside the outer ring of a hermetic seal between the two films. These two flaps for tearing open the plaster preferably cover one another and in the case of a circular plaster they are triangular. The hermetically sealed, i.e., in this case solvent impervious connection between the foils can easily be torn open at the edge of the plaster by means of the two flaps.

This invention also relates to a process for the production of the pharmaceutical adhesive plaster according to the invention in which, as in the case of European publication No. 0 013 606 A 2, two separately produced, external plaster parts are joined together by means of an internal layer of adhesive in such a manner that they can be separated. It is an object of the present invention to disclose such a process which provides for rational mass production of the plasters according to the invention.

According to the invention, this problem is solved by means of the fact that the layer of adhesive is produced as a component of an inner, third part of the plaster which is produced separately from the two outer parts of the plaster and is subsequently firmly joined to them.

The result thereby advantageously achieved is that, although the layer of adhesive must be produced as constituent of a part of the plaster as in the known processes, it need not be produced as part of the container for the active ingredient and as coating of the composite film of this container as in the known process but as contituent of a third part of the plaster, which can be produced independently of the two other plaster parts (leaving aside the question of a membrane), which third plaster part contains the layer of adhesive and can therefore be introduced without any problem of adherence between the two other parts of the plaster and can be equipped with a membrane at its centre if such a membrane does not already form the centre of the third part of the plaster.

In the preferred method of carrying out the process according to the invention for producing the preferred embodiment of the pharmaceutical adhesive plaster according to the invention, the membrane and its third plaster part are produced simultaneously, with the result that the number of process steps required is only half that previously required and the production time for the membrane and third plaster part is halved. This also applies if the membrane is perforated, for example by means of corpuscular radiation, since the third part of the plaster can be perforated at the same time in the same step without any damage to the function of the plaster.

In the preferred method of carrying out the process, the membrane and third part of the plaster are made in a single piece from which a ring conforming to the elevation of the composite film containing the active ingredient is removed to make room for the membrane and the third part of the plaster separately and for the ring along which the covering film is hermetically sealed to the container film so that the medicament is sealed off under the membrane covering the recess in the active ingredient container.

In the preferred method of carrying out the process, the membrane, the elevation in the composite film of active ingredient container and the third part of the plaster are all welded simultaneously to the composite covering film to save in production time. For this purpose, in the preferred method of carrying out the process, welding of the membrane and of the third part of the plaster to the film of the active ingredient container are also carried out simultaneously, in particular in such a manner that the two welding processes, on the composite covering film and on the film of the active ingredient container, are carried out simultaneously.

The invention will now be described in detail with reference to two embodiments of the pharmaceutical adhesive plaster according to the invention illustrated by way of example in the drawings.

BRIEF DESCRIPTION OF THE DRAWINGS

FIG. 1 is a top plan view of the first embodiment, showing the composite covering film;

FIG. 2 is an enlarged view exaggerated in the vertical direction of a central section through the first embodiment before its lower film, containing active ingredient, is joined to the upper, covering film;

FIG. 3 is an equally enlarged but less exaggerated view of the same section taken on the line III—III of FIG. 1 through the first embodiment after the active ingredient container and the composite covering film have been joined together.

DETAILED DESCRIPTION OF A PREFERRED EMBODIMENT

Figure 4:
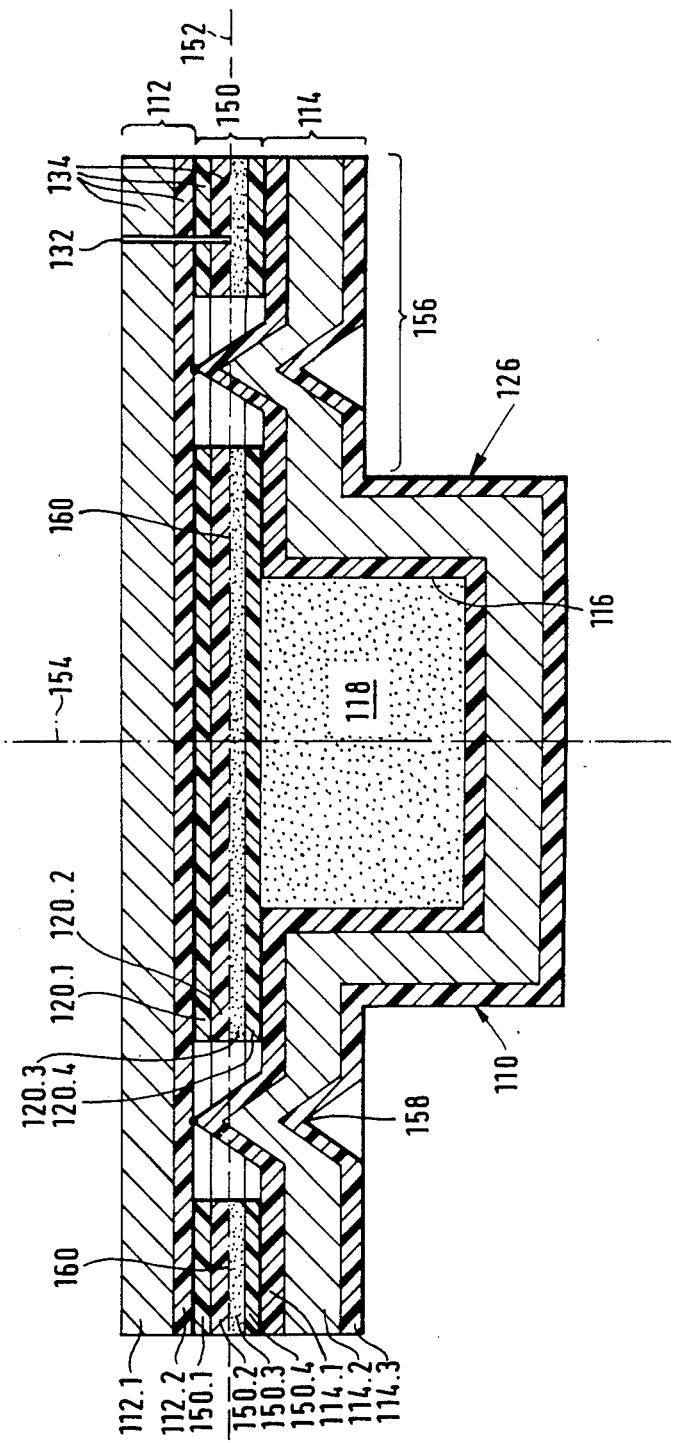
FIG. 4 is a schematic, enlarged view, exaggerated in the vertical direction, of a central section through the second embodiment after all the parts of the plaster have been joined together.

In the first exemplary embodiment, the pharmaceutical adhesive plaster according to the invention illustrated in FIGS. 1 to 3 is composed of two parts joined together, namely a container for the active ingredient 10 and a composite covering film 12. The active ingredient container 10 comprises a composite film 14 forming the outside in which the sequence of layers corresponds to that of the flat composite covering foil 12, i.e. a film of polyamide or thermoplastic polyvinyl chloride (PVC) on the outside and inside and an aluminum foil between these two layers. Both the active ingredient container 10 and the composite covering film 12 have the identical circular contour, as shown in FIG. 1, so that they completely cover one another. The active ingredient container 10 has a circular cylindrical recess 16 at its centre formed, for example, by deep drawing the originally flat composite film 14. Embedded in this recess 16 is a liquid or pasty medicament 18 which fills the recess to its edge and on which is placed a flat, circular, semi-permeable membrane of the active ingredient container 10, which membrane is composed of a synthetic resin layer 22 heat welded to the adjacent PVC film of the composite film 14 and a fibrous web 24 which is connected to the layer 22 and faces the composite covering film 12. The arrangement is such that the membrane 20 completely covers the recess 16 on its opening side but has an external diameter which is smaller than the external diameter of the circular cylindrical outward projection 26 of the container 10, which projection was formed by formation of the recess in the composite film 14. The composite film 14 of the active ingredient container 10 is covered with a layer of adhesive 28 in the form of a circular ring which is concentric to the membrane 20. The external diameter of this ring of adhesive 28 is approximately equal to the external diameter of the recessed composite film and its thickness is approximately equal to the thickness of the membrane 20. The internal diameter of the layer of adhesive 28 is greater than the external diameter of the projection 26 and hence substantially greater than the external diameter of the membrane 20. The layer of adhesive 28 may be a layer of adhesive foam or a band in the form of a ring which is adhesive on both sides.

To join the composite covering film 12 to the active ingredient container 10, the flat covering film 12 is placed on the cup-shaped active ingredient container 10 so that they exactly cover one another. The two parts are then heat welded along an annular zone 30 which, viewed in the radial direction, is situated between the layer of adhesive 28 and the projection 26, so that the PVC layers (laminates) in contact with each other from the composite covering film 12 on the one hand and the composite film 14 of active ingredient container 10 on the other hand fuse together. This heat sealing produces a hermetic seal between the composite covering film 12 and the active ingredient container 10.

For separating the composite covering film 12 from the active ingredient container 10, the covering film has a biconvex piece 34 at the edge which is separated off by means of a separating furrow 32 in the form of a circular arc.

In the preferred, second exemplary embodiment, the pharmaceutical adhesive plaster according to the invention shown in FIG. 4 consists, leaving aside the medicament, of four parts joined together, namely an active ingredient container 110, a composite covering film 112, a plaster ring 150 as third part of the plaster, and a membrane 120. The external circumference of these parts of the plaster and, where present, also the internal circumference are circular with all the centres of the circles lying on the axis of symmetry 154.

The active ingredient container 110 manufactured from a composite film 114 has a central recess 116 which may be conical or which in this example is cylindrical, in which a liquid or pasty medicament 118 is embedded. The medicament fills the recess to the edge, and the recess corresponds to a central, conical or cylindrical, outward projection 126 of the active ingredient container. Viewed in the axial direction from the inside outwards, this active ingredient container comprises an inner thermoplastic layer of synthetic resin 114.1 of polyethylene, a middle metal foil 114.2 of aluminum and an outer thermoplastic synthetic resin layer 114.3 of polyamide, each of which layers is several tenths of a millimeter in thickness. The annular edge 156 of the active ingredient container 110 surrounding the projection 126 lies in a plane perpendicular to the axis 154 and it has a concentric elevation 158 forming a rim which projects towards the composite covering foil 112 and makes contact with it as well as extending into the concentric annular chamber between the membrane 120 and the plaster ring 150. This elevation could be provided on the covering film 112 instead of or in addition being provided on the active container film. If it is provided in addition in the covering film, the two elevations meet halfway.

The composite covering film 112, which is completely planar, is composed of the following layers viewed in the axial direction from the outside inwards: An outer metal foil 112.1 of aluminum and an inner thermoplastic layer of synthetic resin 112.2 consisting of an ionomer.

The completely flat membrane 120 and equally flat plaster ring 150 comprise, both at the same level, a layer of thermoplastic synthetic resin 120.1 and 150.1, respectively, in the form of a spread coat layer welded to the layer 112.2 of the composite film 112, a silicone layer 120.2 and 150.2, respectively, joined to the layers 120.1 and 150.1, respectively, a layer of adhesive 120.3 and 150.3 (outside layer) which can easily be detached from the silicone layer, and a thermoplastic layer of polyethylene 120.4 and 150.4, respectively, which is heat welded to the layer 114.1 of the composite film 114 of active ingredient container and which carries the layer of adhesive. Whereas the layers 120.1 and 150.1 and the layer 150.4 are welded to the layers 112.2 and 114.1, respectively, over the entire surface which forms the outer surface, viewed in the axial direction, and the layers are so arranged that the composite covering film 112, the film of active ingredient container 114 and the plaster ring 150 which is situated between them in the axial direction are in alignment at their external circumferences. The layer 120.4 is only welded to the layer 114.1 at its edge which surrounds the recess 116 and makes no contact with the medicament 118. The elevation 158 of the active ingredient container 110 is heat welded to the layer 112.2 of the composite covering film 112 along a circular ring round the axis 154. The layers 120.3 (adhesive) and 120.4 (polyethylene) are permeable to the active ingredient contained in the medicament 118.

To apply the pharmaceutical adhesive plaster shown in FIG. 4 to the skin, it should be opened along the plane of separation 152 perpendicular to the axis 154 by grasping the composite covering film 112 together with the layers 120.1 and 120.2 of the membrane 120 and the layers 150.1 and 150.2 of the plaster ring 150 at a point on the circumference of the plaster and pulling these layers away from the composite film 114 of active ingredient container together with the layers 120.3 and 120.4 of the membrane 120 and the layers 150.3 and 150.4 of the plaster ring 150. The silicone layers 120.2 and 150.2 readily become detached from the layers of adhesive 120.3 and 150.3 which are subsequently pressed to the skin. The elevation 158 in the active ingredient container 110 constitutes virtually no obstacle in this process since the absolute amount by which it is raised above the plane of separation 152 in the axial direction is of the order of only a few tenths of a millimeter, and the skin can yield by this amount. If necessary, the elevation in the active ingredient container may be arranged to reach only as far as the plane of separation 152, in which case it encounters a corresponding depression in the composite covering film, which is then not flat.

To facilitate the intial stages of opening the plaster, the composite covering film 112 and the layers 150.1 and 150.2 have a common separating furrow 132 which separates off a piece 134 at the margin, which piece adheres to the layer of adhesive 150.3 of the plaster ring 150 and comprises a part consisting of layers 150.1 and 150.2 connected to the composite covering film 112 and another part consisting of layers 150.3 and 150.4 connected to the composite film 114 of active ingredient container, the adhesive layer 150.3 lying with its adhesive surface 160 in contact with the layer 150.2.

This adhesive surfac 160 is continued inwards in the radial direction on the membrane layer 120.3.

Although only preferred embodiments are specifically illustrated and described herein, it will be appreciated that many modifications and variations of the present invention are possible in light of the above teachings and within the purview of the appended claims without departing from the spirit and intended scope of the invention.

What I claim is:

1. A pharmaceutical adhesive plaster comprising two parts jointed together, namely an active ingredient container comprising a composite film and having a shallow recess for containing the medicament, an innermost layer of thermoplastic synthetic resin in the form of a film, and an outer layer or adhesive which is at least one of pressure sensitive and sensitive to the heat of the skin and surrounds the recess in the form of a ring on the opening side of the recess; and a composite covering film comprising an innermost layer of thermoplastic synthetic resin in the form of a film, which is covered with the layer of adhesive and covers the recess of the active ingredient container;

wherein the recess of the active ingredient container is closed by a membrane which is permeable to the active ingredient and is firmly connected to the composite film of the active ingredient container concentrically within the outer layer of the adhesive; and in that the composite covering film is hermetically connected to the composite film of the active ingredient container along a ring extending radially between the membrane and the layer of adhesive;

wherein the membrane is comprised of at least three layers, one of which layers is arranged as a layer of adhesive between the other two layers.

* * * * *